United States Patent [19]

Ichihashi et al.

[11] Patent Number: 5,000,562
[45] Date of Patent: Mar. 19, 1991

[54] OPHTHALMIC DISEASE DETECTION METHOD AND APPARATUS

[75] Inventors: Tadashi Ichihashi; Koichi Akiyama, both of Tokyo, Japan

[73] Assignee: Kowa Company Ltd., Japan

[21] Appl. No.: 210,811

[22] Filed: Jun. 24, 1988

[30] Foreign Application Priority Data

Jun. 25, 1987 [JP] Japan ............................... 62-156660
Jun. 25, 1987 [JP] Japan ............................... 62-156661

[51] Int. Cl.⁵ ............................................... A61B 3/10
[52] U.S. Cl. .................................... 351/221; 351/205; 351/214
[58] Field of Search ....................... 351/205, 214, 221; 128/633; 606/4

[56] References Cited

U.S. PATENT DOCUMENTS 4,852,987 8/1989 Lohmann ............................ 351/221

FOREIGN PATENT DOCUMENTS 225072 6/1987 European Pat. Off. ............ 351/221

Primary Examiner—Rodney B. Bovernick
Attorney, Agent, or Firm—Bruce L. Adams; Van C. Wilks

[57] ABSTRACT

An apparatus for detecting ophthalmic diseases such as an inflammation in a patient's eye which includes means for focusing a laser beam at a selected spot in the eye. The light scattered from the eye is photoelectrically detected and converted into an electrical signal which is subsequently used to determine the protein concentration essential to ophthalmic disease detection in the patient's eye. The laser beam is deflected vertically and horizontally. The electrical signal derived from the vertical scanning is compared with the other electrical signals from the horizontally shifted scanning of the laser beam to remove noises from the electrical signal.

7 Claims, 5 Drawing Sheets

OPHTHALMIC DISEASE DETECTION METHOD AND APPARATUS

BACKGROUND OF THE INVENTION

1. Field of the Invention

This invention relates to a method and apparatus for detecting ophthalmic diseases in a patient's eye, and more particularly to a method and apparatus for detecting ophthalmic diseases in which laser light is radiated via an optical system at one spot in the camera oculi of the patient's eye, particularly in the anterior chamber thereof, and the laser light scattered therefrom is analyzed to measure the protein concentration for ophthalmic disease detection in the camera oculi.

2. Description of the Prior Art

The camera oculi is comprised of the camera oculi anterior (anterior chamber) and the camera oculi posterior (posterior chamber). The camera oculi anterior is defined by a space surrounded by the rear surface of the cornea, a part of the ciliary body, the iris, and the front surface of the crystalline lens, while the camera oculi posterior is defined by a space surrounded by the rear surface of the iris, the inner surface of the ciliary body, and the front surface of the crystalline lens. The camera oculi is filled with transparent humor aqueous, which has chemical and physical characteristics that are different from those of lymphatic liquid and has a close relation with the metabolism of the cornea or crystalline lens. The humor aqueous contains proteins the increase of which causes turbidity in the camera oculi when it becomes inflamed.

In this respect, the measurement of protein concentration in the camera oculi of the patient's eye is of great importance in determining whether the camera oculi is inflamed, that is, whether a blood-aqueous barrier is functioning normally or not.

To measure the protein concentration in the camera oculi, a slit lamp microscope is very often used to determine the turbidity by grading via the naked eye. This is, however, disadvantageous because the judgment depends upon the person who performs the measurement.

On the other hand, a photographic measuring method has been developed to make a quantitative measurement of the protein concentration. This method is, however, highly complicated to analyze, and is thus very difficult to apply in a clinical examination.

To overcome this problem, an apparatus for detecting ophthalmic diseases has been proposed which includes means for focusing a laser beam at a selected spot in the camera oculi of an eye. In the apparatus, the light scattered from the eye is photoelectrically detected and converted into an electrical signal which is subsequently used to determine the protein concentration essential to ophthalmic disease detection in the camera oculi of the patient's eye. See, for example, Japanese Patent Laying-open No. 120834/87.

However, there have been problems with conventional methods, such as that the volume of the part to be measured being limited adversely affects the precision of the measurement. When measuring scattered laser light, light reflecting and scattering from the cornea, the iris, the crystalline lens, including artificial crystalline lenses employed following a white cataract operation, and floating cells and the like, shows up as noise in the scattered laser light and in the measurement site in the anterior chamber thereby degrading measurement accuracy and preventing measured values from being reproduced.

SUMMARY OF THE INVENTION

It is therefore an object of the present invention to provide a method and apparatus for detecting ophthalmic diseases which enable the protein concentration in a patient's eye to be measured precisely and easily.

Another object of the present invention is to provide a method and apparatus for detecting ophthalmic diseases which enable the noise from reflected or scattered light which may impinge on the spot to be measured in a patient's eye to be reduced or removed.

An apparatus for detecting ophthalmic diseases according to the present invention comprises a laser source for producing a laser beam, a laser beam projector for projecting the laser beam, means for focusing the laser beam at a selected spot in a patient's eye, means for deflecting the laser beam in vertical and horizontal directions to scan an area including the spot in the patient's eye, means for receiving light scattered by a floating particle in the patient's eye and photoelectrically converting it into an electrical signal, a mask disposed in front of the photoelectric converting means and formed thereon with a slit having a predetermined width to limit the scattered light that impinges on the photoelectric converting means, and means for processing the electrical signal to evaluate ophthalmic diseases in the patient's eye. The laser beam is deflected in a first direction and in a second direction perpendicular thereto to scan an area in the patient's eye that includes the spot. The scanning in the first direction is repeated with the laser beam shifted in the second direction for each scanning along the first direction. The electrical signal at a position along the first direction is compared with other signals at the same position derived from the scanning of the laser beam shifted in the second direction to remove noise from the electrical signal.

Thus, in accordance with the present invention the laser beam converged on a predetermined spot in the eye is scanned horizontally and vertically and the scattered laser light is detected, so it is therefore possible to increase the measurement volume in the eye, thereby improving the precision of the measurement.

With the above arrangement, because the measurement location in the eye changes with each scan made in the vertical direction (first direction), the measured values of scattered light constituted of noise produced by floating cells and the like differ from scan to scan. As such, the influence of such noise produced by floating cells, for example, can be removed by comparing measured values obtained at the same position in the vertical direction during vertical scanning and selecting the minimum value, for instance.

Preferably, a memory is provided to store the electrical signals derived from the deflection of the laser beam in the first and second directions.

In a preferred embodiment of the present invention, the laser beam is so deflected that its vertical scanning width is made larger or smaller than the width of the slit on the mask. In the case described herein the scanning width of the mask is made larger than the diameter of the laser beam.

BRIEF DESCRIPTION OF THE DRAWINGS

The objects and features of the present invention will become more apparent from a consideration of the following detailed description taken in conjunction with the accompanying drawings in which.

DETAILED DESCRIPTION OF THE PREFERRED EMBODIMENTS

The invention will now be described in detail with reference to the drawings.

Figure 1:
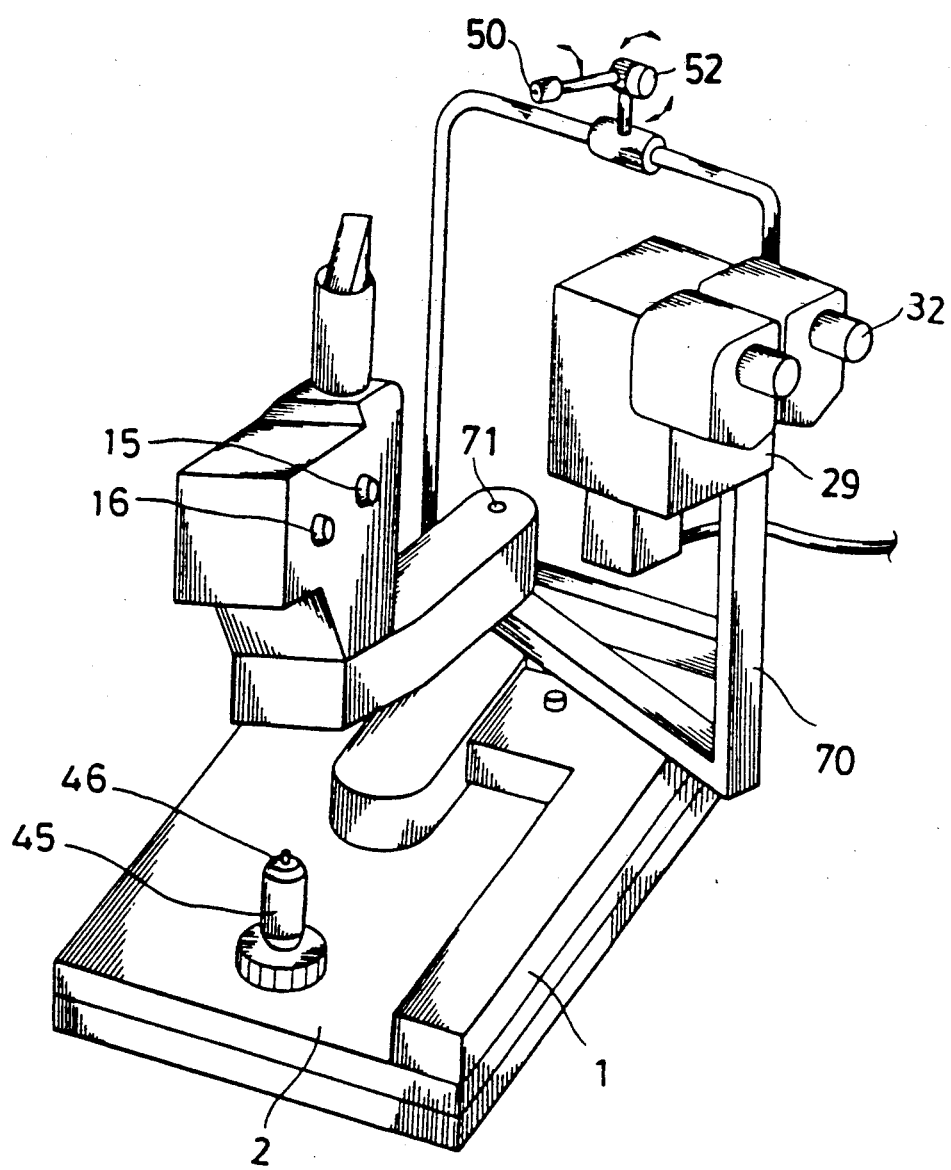
FIG. 1 is a perspective view of an apparatus according to the present invention.
Figure 2:
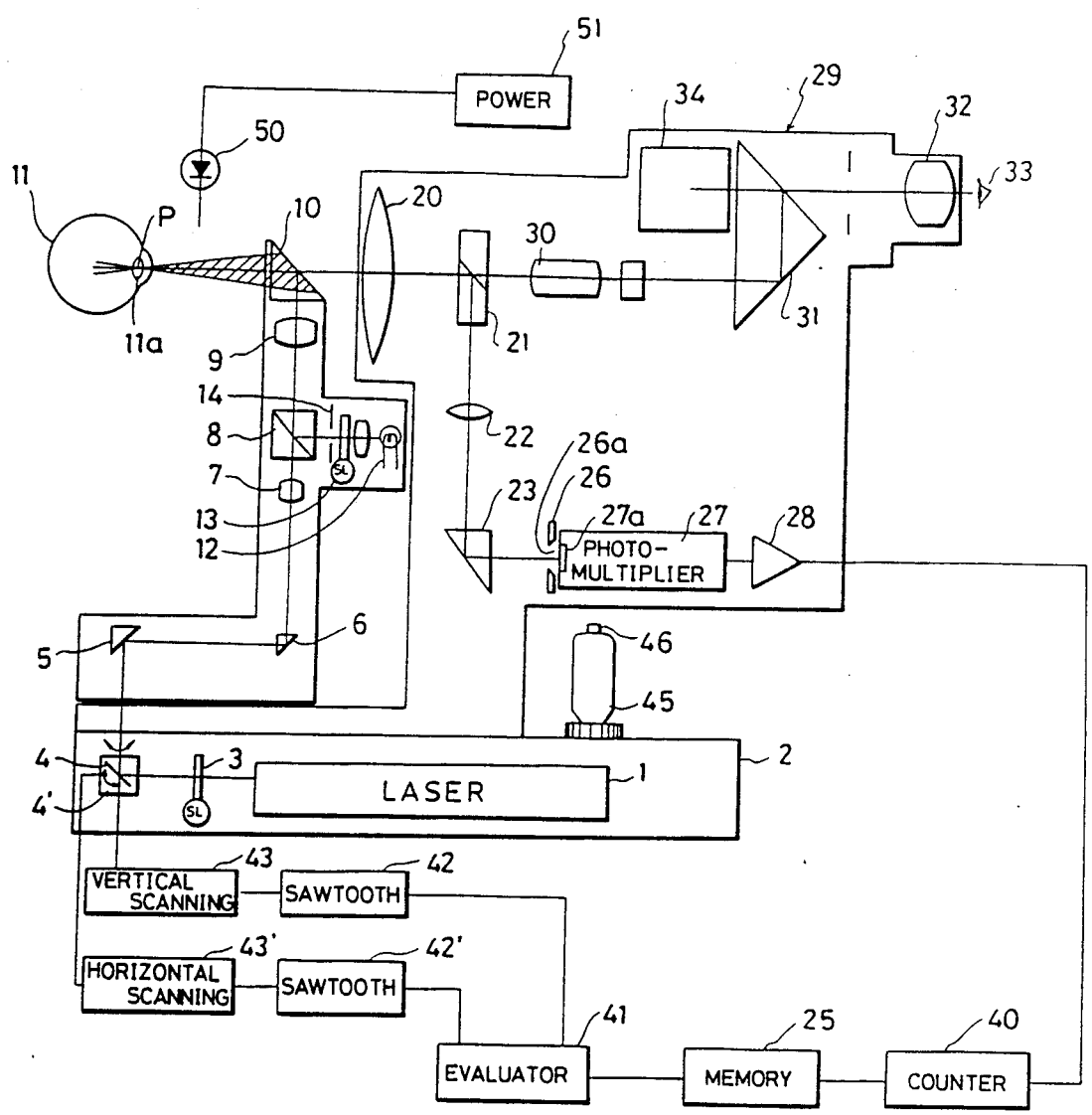
FIG. 2 is a drawing showing the arrangement of the optical system of the apparatus.
Figure 3:
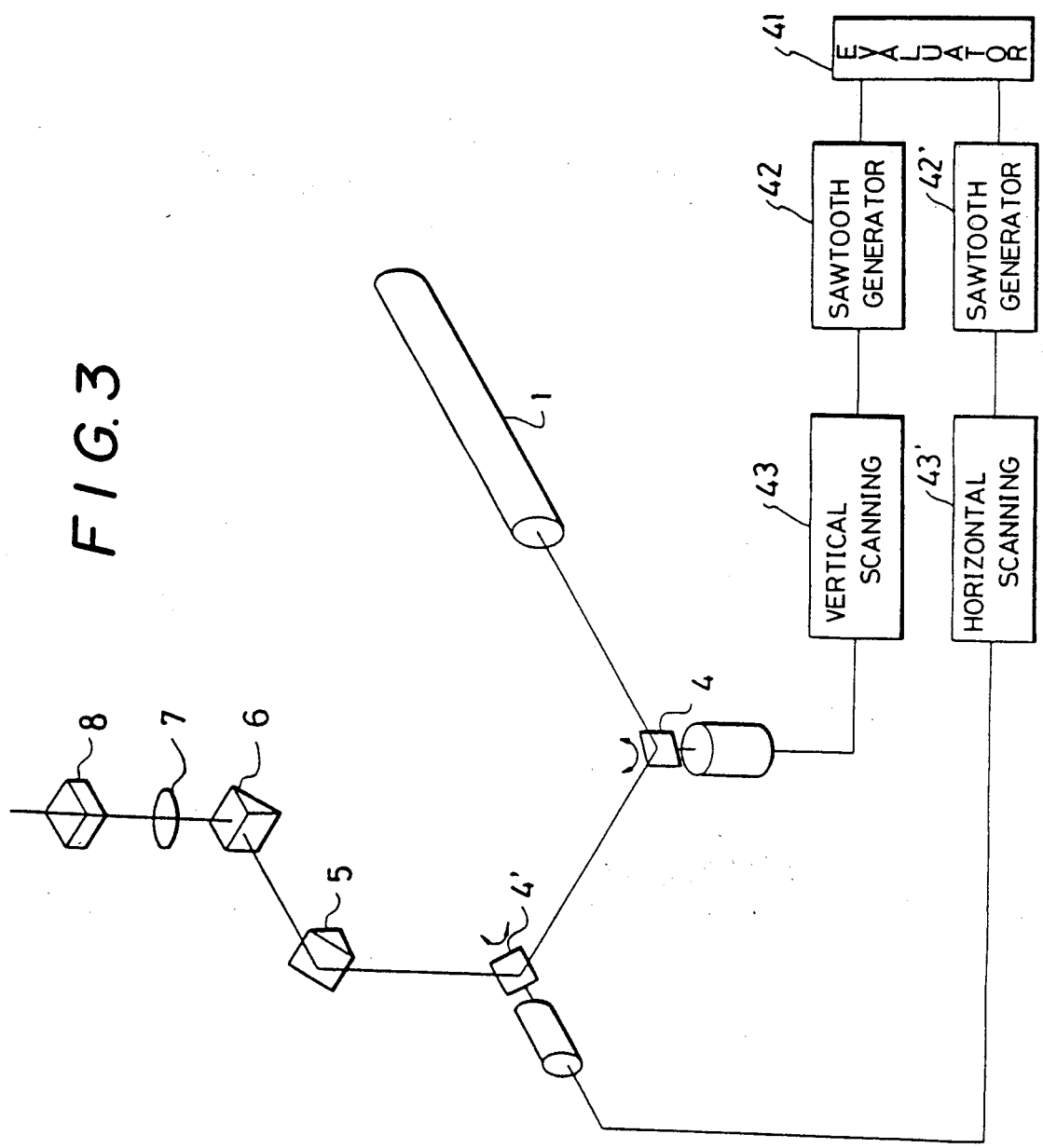
FIG. 3 is a drawing showing the arrangement of the laser beam scanning optical system of the apparatus.

In FIGS. 1 to 3, which show an arrangement of the ophthalmic disease detection apparatus according to the present invention, reference numeral 1 denotes a laser light source, such as, for example, a helium-neon or argon laser source. The laser light source 1 is disposed on a stand 2. Light from the laser light source 1 is passed through a laser beam filter 3 and via a vertical scanning mirror 4, a horizontal scanning mirror 4', prisms 5 and 6, a lens 7, a beam splitter 8, a condenser lens 9 and a prism 10 to converge on the eye under examination 11 at a spot in the anterior chamber 11a thereof.

The laser beam projector is provided with a slit light source 12. Light from the slit light source 12 passes via a slit light shutter 13 and a slit 14 and goes via the beam splitter 8, lens 9 and prism 10 to form a slit image on the anterior chamber 11a. With the light from the laser light source being converged to a spot, this slit image is for illuminating the surrounding area to facilitate confirmation of the position of the spot of converged light.

The width and length of the slit 14 can be adjusted by an adjusting knob 15 and a switching knob 16, respectively, which are shown in FIG. 1.

A portion of the laser light scattered from the measuring spot in the anterior chamber 11a passes through an objective lens 20 of a detection section 29 and is split by a beam splitter 21. One part of the light thus split passes through a lens 22, a prism 23 and a slit mask 26 provided with a slit 26a and impinges on a photomultiplier 27 used as a photoelectric converter. The other part of the scattered light split by the beam splitter 21 passes via a lens 30 and prisms 31 and 34 to an eyepiece 32 by means of which an examiner 33 can carry out observations.

The output from the photomultiplier 27 is passed through an amplifier 28 and is input to a counter 40 and the intensity of the scattered light detected by the photomultiplier is counted as numbers of pulses per unit time period. The output of the counter 40, i.e., the number of samplings or the total pulse count, is stored in a memory 25 allocated for each unit time period. The data stored in the memory 25 is processed by an evaluating device 41 which, as explained below, computes a count of floating matter in the anterior chamber.

FIG. 3 shows details of the vertical and horizontal scanning mirrors 4 and 4'. Under the control of the evaluating device 41, the mirrors are caused to swing vertically or horizontally by means of sawtooth generators 42 and 42' and vertical and horizontal scanning mirror drive circuits 43 and 43', causing the laser beam to scan vertically and horizontally, thereby enabling the spot of laser light to be moved vertically and horizontally within the anterior chamber. The scanning of the spot of laser light is arranged so that the scanning runs do not exceed the width, in the vertical direction, of the slit 26a with the scanning center set to be the center of the slit.

In accordance with this invention, an eye fixation light 50 constituted of a light-emitting diode or the like powered by electricity supplied from a power source 51 is disposed at a position that permits the examiner to fix the patient's eye. The light selected for the eyed fixation light 50 is of a different color than the light of the laser light source 1. For example, when the light from the laser light source is red, a green light is selected. The eye fixation light 50 can be turned in the direction indicated by the arrow by means of a link mechanism 52 to enable it to be adjusted so that it is always in an optimum position with respect to the patient's eye.

Provided on the base 2 is an input means, such as a joystick 45 equipped with a push-button 46, and this can be operated to insert the laser filter 3 and the slit light shutter 13 into, or retract these elements from, the respective optical system.

The operation of the apparatus arranged thus will now be described. In conducting the measurement, the slit light source 12 is activated and an image of the slit 14 is formed, via the beam splitters 8 and 10 and the lens 9, and the prism 10, on a part of the anterior chamber 11a that includes the measurement point P. Following this, light from the laser light source 1 is converged on the measuring point P via the optical system.

A portion of the light scattered from the measuring point P is simultaneously directed by the beam splitter 21 to the examiner 33 for observation and through a lens 22, a prism 23 and the mask 26 to impinge on the photomultiplier 27.

Under the control of the evaluating device 41, scanning is performed by the vertical and horizontal scanning mirrors 4 and 4' by means of the sawtooth generators 42 and 42' and vertical and horizontal scanning mirror drive circuits 43 and 43'.

Figure 4:
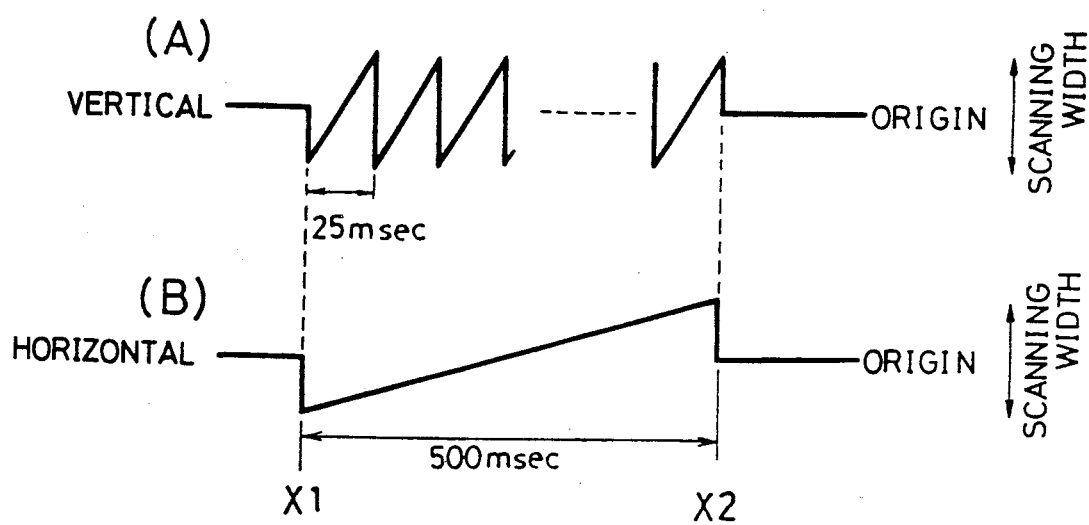
FIGS. 4 (A) and 4(B) are laser beam scanning signal waveforms.

The sawtooth generators 42 and 42' each produce the type of signal shown in FIGS. 4 (A) and 4 (B) for the scanning of the laser beam. In the drawing X1 indicates the starting point of the measurement and X2 the completion of the measurement. If the horizontal scanning frequency is $H_f$ and the vertical scanning frequency is $V_f$ and the number of vertical scans or scanning runs is N, then $H_f = V_f/N$.

Figure 5:
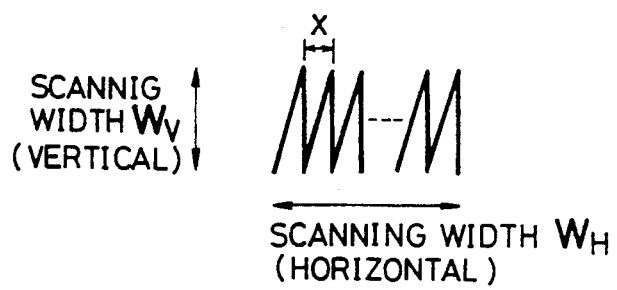
FIG. 5 is an explanatory drawing illustrating the scanning path of the laser beam, as viewed from the perspective of the laser beam projector.

The vertical and horizontal scanning mirrors 4 and 4' are scanned in accordance with the signal waveforms, causing the laser beam to perform scanning with measurement point P at the center of the scan. FIG. 5 shows the actual scanning state as seen from the laser beam projector. In order to remove noise components formed by light reflections in the eye and efficiently receive signals derived from the scattered light, the width $W_v$ of the vertical scan is set smaller than the vertical width of the slit 26a.

Thus, the photomultiplier 27 receives the incident scattered laser light via the slit 26a, detects the intensity of the light that has been scattered by floating particles in the anterior chamber 11a and converts this into a corresponding series of pulses which are counted by the counter 40 as number of pulses per unit time period, and the count values are then stored in the memory 25 allocated for each unit time period.

Figure 6:
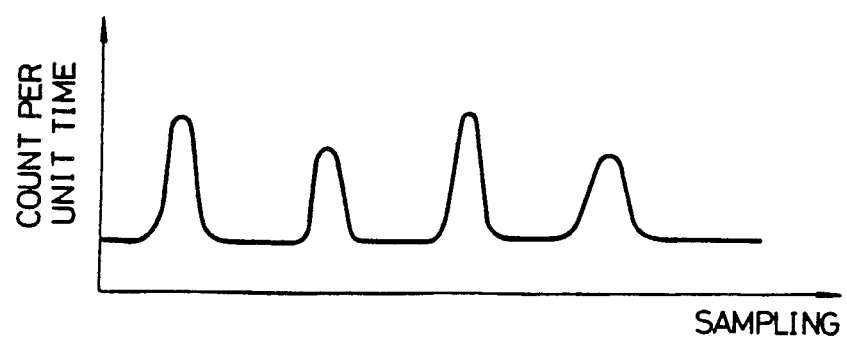
FIG. 6 is an explanatory graph showing peaks in light scattered by floating matter.

Because the floating particles in the anterior chamber which are the object of the measurement are larger than several micrometers in diameter, when the laser beam passes across a floating particle the scattered-light intensity registers a peak. Therefore, if the measurement of floating particles is carried out with the measurement unit time period set so as to be shorter than the time required for the laser to traverse a floating particle, and the count data stored in the memory 25 is represented as a time-series, the count values will only show an increase where the laser beam traverses a floating particle, thereby producing the kind of waveform illustrated in FIG. 6. In FIG. 6, each peak was produced by light scattered by a floating particle. Counting the peaks by means of the evaluating device 41 enables the measurement of the number of floating particles within the anterior chamber space that is scanned vertically and horizontally by the laser beam.

Moreover, if the laser beam is moving at a constant velocity when it traverses a floating particle and the diameter of the laser beam is known beforehand, the size of the particles can be calculated from the width of the peak. To prevent the same particle being counted twice, the scanning waveform is given the sawtooth shape shown in FIG. 5 and the horizontal scanning width is set so that the horizontal pitch or peak gap x between successive scanning runs is larger than the diameter of the laser beam.

Figure 7:
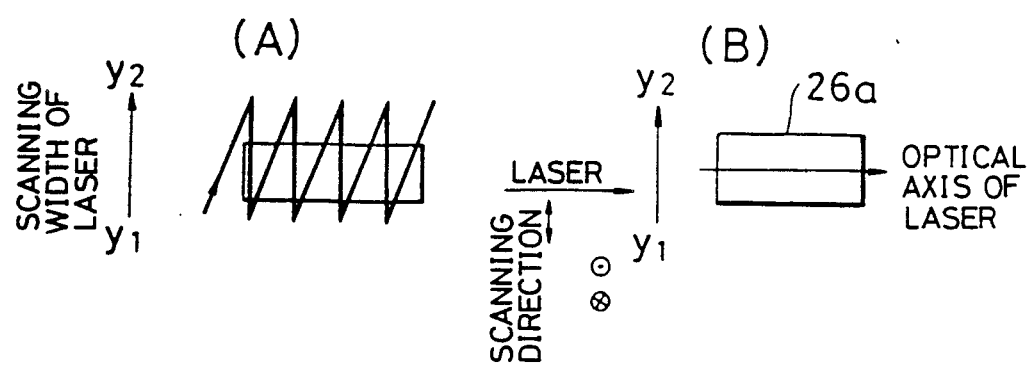
FIGS. 7 (A) and 7 (B) are explanatory drawings illustrating the scanning path of the laser beam, as viewed from the perspective of the laser beam projector, according to another embodiment of the present invention.

In the embodiment illustrated in FIG. 7, each of the laser beam waveforms is shown. In order to remove noise components formed by light reflections in the eye and efficiently receive signals derived from the scattered light, the width y1-y2 of the vertical scan is set to be larger than the vertical width of the slit 26a.

In the case of this embodiment, the photomultiplier 27 receives the incident scattered laser light via the slit 26a, detects the intensity of the light that has been scattered by protein particles in the anterior chamber 11a and converts this into a corresponding series of pulses which are counted by the counter 40 as a number of pulses per unit time period, and the count values are then stored in the memory 25 allocated for each unit time period.

In this case, with reference to FIG. 7, the laser beam scans once in the vertical direction from y1 to y2 and the value obtained from the scan is stored in a first memory area in the memory 25. Next, a horizontal scan is performed and the value obtained from the next vertical scan is stored in a second memory area. This sequence is repeated, with the signal data resulting from the nth vertical scan being stored in the nth memory area.

Figure 8:
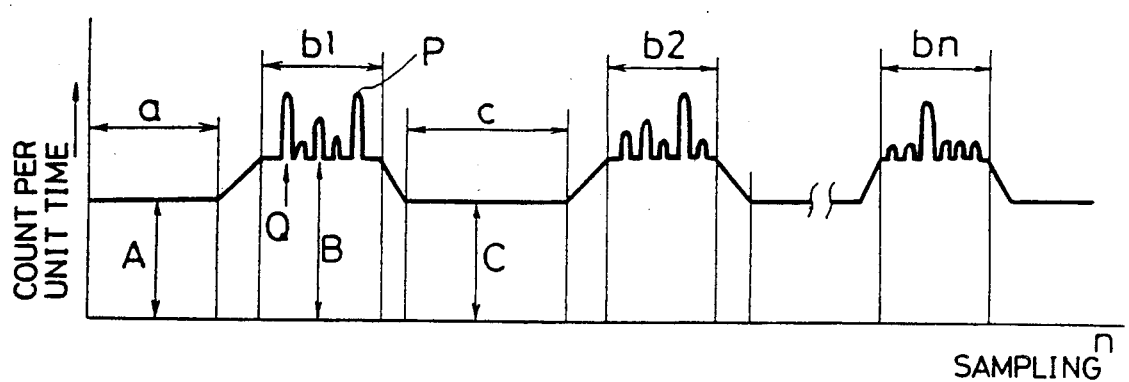
FIG. 8 is an illustration of a signal waveform depicting time-series data of measured values obtained in the case of the embodiment of FIG. 7.

When count values have thus been stored in the memory areas, if these count values stored in the memory 25 are arranged in the form of a time series, the result would be as shown in FIG. 8. With reference to FIG. 8, a and c are intervals when the laser beam is not impinging within the slit 26a, and indicate the inclusion of noise components produced by intra-ocular light reflections and scattering.

A and C are taken as average count values in the memory 25 for the intervals a and c. Also included as noise in A and C is the dark current of the photomultiplier 27. Such noise components fluctuate from measurement to measurement, which degrades the consistency of the measured values.

Interval b is an interval during which the scattered laser light is included via the slit 26a, and includes signal components corresponding to the protein concentration in the anterior chamber, and noise components of light reflected and scattered by floating cells and the like. Thus, in accordance with the present invention the laser beam is scanned horizontally so that the eye portion being measured changes with each vertical scan, count-value peaks P resulting from noise components are located in intervals $b_1$, $b_2$, $b_n$ and are each different. Therefore, by comparing count values per unit time period for the same position on the vertical scans (position Q, for example) and selecting the minimum value for each position in the vertical direction, it becomes possible to remove noise components. The noise components can be removed with even greater accuracy by increasing the number of vertical scans.

By means of the evaluating device 41, the noise components in each of the intervals $b_1$–$b_n$ are thus removed, an average value B for the interval is obtained and data values A or C are deducted therefrom to thereby extract only the effective signal components and calculate the protein concentration in the anterior chamber.

While the invention has been described with reference to preferred embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

We claim:

1. An apparatus for detecting for ophthalmic diseases in a patient's eye comprising:
    a laser source for producing a laser beam having a given diameter;
    a laser beam projector for projecting said laser beam;
    means for focusing said laser beam at a selected spot in said patient's eye;
    means for deflecting said laser beam in vertical and horizontal directions according to a sawtooth scanning waveform to scan an area including said spot in the patient's eye, the sawtooth waveform having a horizontal pitch that is larger than the diameter of the laser beam;
    photoelectric converting means for receiving light scattered by a floating particle in said patient's eye and photoelectrically converting it into an electrical signal;
    a mask disposed in the front of said photoelectric converting means and having a slit having a predetermined width to limit the scattered light that impinges on said photoelectric converting means; and means for processing said electrical signal to evaluate to ophthalmic diseases in the patient's eye.

2. An apparatus as set forth in claim 1, wherein said photoelectric converting means includes means for converting the scattered light into an electrical signal composed of a series of pulses whose number per unit time period is proportional to the intensity of scattered light and said unit time period is set so as to be shorter than the time required for the laser beam to traverse said floating particle.

3. An apparatus as set forth in claim 1, wherein said laser beam is so deflected that its vertical scanning width is made smaller than the slit width on said mask.

4. A method for detecting for ophthalmic diseases in a patient's eye, in which a laser beam is projected at a selected spot in said patient's eye, and light scattered therefrom is received through a mask onto a photoelectrical converter for conversion into an electrical signal, comprising the steps of:

deflecting said laser beam in a first direction to scan an area including said spot in the patient's eye;

repeating the scanning in said first direction with said laser beam shifted in a second direction perpendicular to said first direction for each scanning;

comparing the electrical signal at a position along said first direction with other electrical signals at the same position derived from the scanning of said laser beam shifted in the second direction to remove noises from said electrical signal; and processing said electrical signal to evaluate for ophthalmic diseases in the patient's eye.

5. A method as set forth in claim 4, wherein said laser beam is so deflected that its vertical scanning width is made greater than the slit width on said mask.

6. An apparatus for detecting for ophthalmic diseases in a patient's eye comprising:

a laser source for producing a laser beam;

a laser beam projector for projecting said laser beam;

means for deflecting said laser beam in a first direction to scan an area including said spot in the patient's eye;

means for deflecting said laser beam in a second direction perpendicular to said first direction;

photoelectric converting means for receiving light scattered from said patient's eye and photoelectrically converting it into an electrical signal;

a mask disposed in the front of said photoelectric converting means and having a slit having a predetermined width to limit the scattered light that impinges on said photoelectric converting means;

means for processing said electrical signal to evaluate for ophthalmic diseases in the patient's eye;

means for storing said electrical signal derived from said scanning in said first direction for each scanning in said second direction; and means for comparing said electrical signals derived from said scanning in said first direction for each scanning in said second direction to remove noises contained in said electrical signals.

7. An apparatus as set forth in claim 6, wherein said laser beam is so deflected that its vertical scanning width is made greater than the slit width on said mask.

* * * * *